US012629391B1

(12) United States Patent (10) Patent No.: US 12,629,391 B1

Omran et al. (45) Date of Patent: May 19, 2026

(54) METHOD OF TREATING CANCER CELLS USING COBALT OXIDE/CALCIUM SILICATE@GRAPHITIC CARBON NITRIDE (CoO/CASIO3@G-C3N4) NANOCOMPOSITE

(71) Applicant: IMAM MOHAMMAD IBN SAUD ISLAMIC UNIVERSITY, Riyadh (SA)

(72) Inventors: Mohamed Khairy Abdel Fattah Omran, Riyadh (SA); Babiker Yagoub Elhadi Abdulkhair, Riyadh (SA)

(73) Assignee: IMAM MOHAMMAD IBN SAUD ISLAMIC UNIVERSITY, Riyadh (SA)

( * ) Notice: Subject to any disclaimer, the term of this patent is extended or adjusted under 35 U.S.C. 154(b) by 0 days.

(21) Appl. No.: 19/256,101

(22) Filed: Jun. 30, 2025

(51) Int. Cl.
*A61K 33/24* (2019.01)
*A61K 9/16* (2006.01)
*A61P 35/00* (2006.01)

(52) U.S. Cl.
CPC ................ *A61K 33/24* (2013.01); *A61K 9/16* (2013.01); *A61P 35/00* (2018.01)

(58) Field of Classification Search
CPC .......... A61K 33/00; A61K 33/24; A61K 9/00; A61K 9/16; A61P 35/00
See application file for complete search history.

(56) References Cited

FOREIGN PATENT DOCUMENTS

| CN | 106746659 A | 5/2017 |
| CN | 115463683 A | 12/2022 |
| KR | 10-2022-0021747 A | 2/2022 |

OTHER PUBLICATIONS

Yuxiang, Zhu, et al., "Tunable Type I and II heterojunction of CoOx nanoparticles confined in g-C3N4 nanotubes for photocatalytic hydrogen production", Applied Catalysis B: Environmental, vol. 244, May 5, 2019, pp. 814-822, Excerpts only, 7 pages.

H.H.A. Sherif, et al., "The impact of cobalt oxide additions and heat treatment on wollastonite for magnetic applications", Ceramics International, vol. 50, Issue 22, Part B, Nov. 15, 2024, pp. 46962-46972, Excerpts only, 7 pages.

*Primary Examiner* — D. L. Jones
(74) *Attorney, Agent, or Firm* — Oblon, McClelland, Maier & Neustadt, L.L.P.

(57) ABSTRACT

A method of treating cancer cells includes contacting the cancer cells with a $CoO/CaSiO_3@g-C_3N_4$ nanocomposite material. The $CoO/CaSiO_3@g-C_3N_4$ nanocomposite material includes hexagonal metal oxide nanoparticles comprising a CoO phase and a $CaSiO_3$ phase dispersed on a matrix of $g-C_3N_4$ nanosheets. The hexagonal metal oxide nanoparticles have an average particle diameter in a range from 340 to 440 nm. The $CoO/CaSiO_3@g-C_3N_4$ nanocomposite material has a percent inhibition for Human Breast Carcinoma (MCF-7) cells at least 55% inhibition in an in-vitro cellular viability assay.

19 Claims, 4 Drawing Sheets

1

METHOD OF TREATING CANCER CELLS USING COBALT OXIDE/CALCIUM SILICATE@GRAPHITIC CARBON NITRIDE (CoO/CASIO3@G-C3N4) NANOCOMPOSITE

BACKGROUND

Technical Field

The present disclosure is directed to a method of treating cancer cells and, more particularly, relates to a method of treating cancer cells using a nanocomposite including cobalt oxide (CoO), calcium silicate ($CaSiO_3$), and graphitic carbon nitride ($g\text{-}C_3N_4$)

Description of Related Art

The "background" description provided herein is for the purpose of generally presenting the context of the disclosure. Work of the presently named inventors, to the extent it is described in this background section, as well as aspects of the description which may not otherwise qualify as prior art at the time of filing, are neither expressly nor impliedly admitted as prior art against the present disclosure.

Worldwide, cancer is the leading cause of death and disability due to its complicated pathological process. Cytotoxicity, low therapeutic indices, low bioavailability, insolubility, high dose requirements, non-specific targeting, and the development of multiple drug resistance are all problems with conventional chemotherapy. Overexpression of drug efflux transporters, anoxic conditions, and abnormal apoptotic pathways are all components of cancer treatment resistance. To address these differences, many nanomaterials (NMs) have gained interest as potential anticancer agents [Mandal, A., Nanomaterials as targeted delivery system of therapeutics for inhibition of cancer, *Journal of Drug Delivery and Therapeutics*, 2023, 13, 12, 201-223; and Algethami, F., et al., Fast fabrication of bismuth oxyiodide/carbon-nanofibers composites for efficient antiproliferation of liver and breast cancer cells, *Zeitschrift für anorganische und allgemeine Chemie*, 2021, 647, 19, 1921-1929]. Size, shape, and surface adjustment of NMs improves targeting efficiency and circulation time, which in turn increases the targeting potential of anticancer cargos. NMs can boost therapeutic efficacy by controlled release by targeting cargos to cancer sites through encapsulation or coupling with ligands. In cancer treatments, NMs are often used to target cancer cells and tumor microenvironments primarily through stimuli-responsive targeting or by modifying their surfaces with targeting ligands like transferin, integrins, sugar, folic acid, and antibodies to improve tissue targeting recognition and internalization.

Although several nanomaterials have been used in the past for cancer treatment, there still exists a need to develop nanomaterials with improved selectivity and cytotoxic activity against cancer cells.

SUMMARY

In an exemplary embodiment, a method of treating cancer cells is described. The method includes contacting the cancer cells with a $CoO/CaSiO_3@g\text{-}C_3N_4$ nanocomposite material, wherein the $CoO/CaSiO_3@g\text{-}C_3N_4$ nanocomposite material comprises hexagonal metal oxide nanoparticles comprising a CoO phase and a $CaSiO_3$ phase dispersed on a matrix of $g\text{-}C_3N_4$ nanosheets, wherein the hexagonal metal oxide nanoparticles have an average particle diameter in a range from 340 to 440 nm, and wherein the CoO/$CaSiO_3@g\text{-}C_3N_4$ nanocomposite material has a percent inhibition for human Breast carcinoma (MCF-7) cells of at least 55% inhibition in an in-vitro cellular viability assay.

In some embodiments, the $CoO/CaSiO_3@g\text{-}C3N_4$ nanocomposite material has a percent inhibition for MCF-7 cells of at least 60% inhibition in an in-vitro cellular viability assay.

In some embodiments, the $CoO/CaSiO_3@g\text{-}C3N_4$ nanocomposite material has a percent inhibition for MCF-7 cells of at least 65% inhibition in an in-vitro cellular viability assay.

In some embodiments, the $CoO/CaSiO_3@g\text{-}C_3N_4$ nanocomposite material has a percent inhibition for MCF-7 cells of at least 70% inhibition in an in-vitro cellular viability assay.

In some embodiments, the $CoO/CaSiO_3@g\text{-}C_3N_4$ nanocomposite material has a percent inhibition for MCF-7 cells of at least 75% inhibition in an in-vitro cellular viability assay.

In some embodiments, the $CoO/CaSiO_3@g\text{-}C_3N_4$ nanocomposite material has a percent inhibition for MCF-7 cells of 77% inhibition in an in-vitro cellular viability assay.

In some embodiments, the $CoO/CaSiO_3@g\text{-}C_3N_4$ nanocomposite material has a percent inhibition for Human Hepatocellular Carcinoma (HepG-2) cells of at least 60% inhibition in an in-vitro cellular viability assay.

In some embodiments, the $CoO/CaSiO_3@g\text{-}C_3N_4$ nanocomposite material has a percent inhibition for HepG-2 cells of at least 65% inhibition in an in-vitro cellular viability assay.

In some embodiments, the $CoO/CaSiO_3@g\text{-}C_3N_4$ nanocomposite material has a percent inhibition for HepG-2 cells of at least 70% inhibition in an in-vitro cellular viability assay.

In some embodiments, the $CoO/CaSiO_3@g\text{-}C_3N_4$ nanocomposite material has a percent inhibition for HepG-2 cells of at least 75% inhibition in an in-vitro cellular viability assay.

In some embodiments, the $CoO/CaSiO_3@g\text{-}C_3N_4$ nanocomposite material has a percent inhibition for HepG-2 cells of 76% inhibition in an in-vitro cellular viability assay.

In some embodiments, the hexagonal metal oxide nanoparticles have an average particle diameter in a range from 370 to 410 nm.

In some embodiments, the hexagonal metal oxide nanoparticles have an average particle diameter in a range from 380 to 400 nm.

In some embodiments, the $CoO/CaSiO_3@g\text{-}C_3N_4$ nanocomposite material has a BET surface area of at least 20 $m^2 \cdot g^{-1}$.

In some embodiments, the $CoO/CaSiO_3@g\text{-}C_3N_4$ nanocomposite material has a BET surface area of at least 25 $m^2 \cdot g^{-1}$.

In some embodiments, the $CoO/CaSiO_3@g\text{-}C_3N_4$ nanocomposite material has a BET surface area of at least 30 $m^2 \cdot g^{-1}$.

In some embodiments, the $CoO/CaSiO_3@g\text{-}C_3N_4$ nanocomposite material has a pore volume of at least 0.10 $cm^3 \cdot g^{-1}$.

In some embodiments, the $CoO/CaSiO_3@g\text{-}C_3N_4$ nanocomposite material has a pore volume of at least 0.15 $cm^3 \cdot g^{-1}$.

In some embodiments, the $CoO/CaSiO_3@g\text{-}C_3N_4$ nanocomposite material has a pore volume of at least 0.195 $cm^3 \cdot g^{-1}$.

3

In some embodiments, the $CoO/CaSiO_3@g\text{-}C_3N_4$ nanocomposite material has an average pore diameter of 21.82 nm.

The foregoing general description of the illustrative embodiments and the following detailed description thereof are merely exemplary aspects of the teachings of this disclosure and are not restrictive.

BRIEF DESCRIPTION OF THE DRAWINGS

A more complete appreciation of this disclosure and many of the attendant advantages thereof will be readily obtained as the same becomes better understood by reference to the following detailed description when considered in connection with the accompanying drawings, wherein.

DETAILED DESCRIPTION

Figure 1:
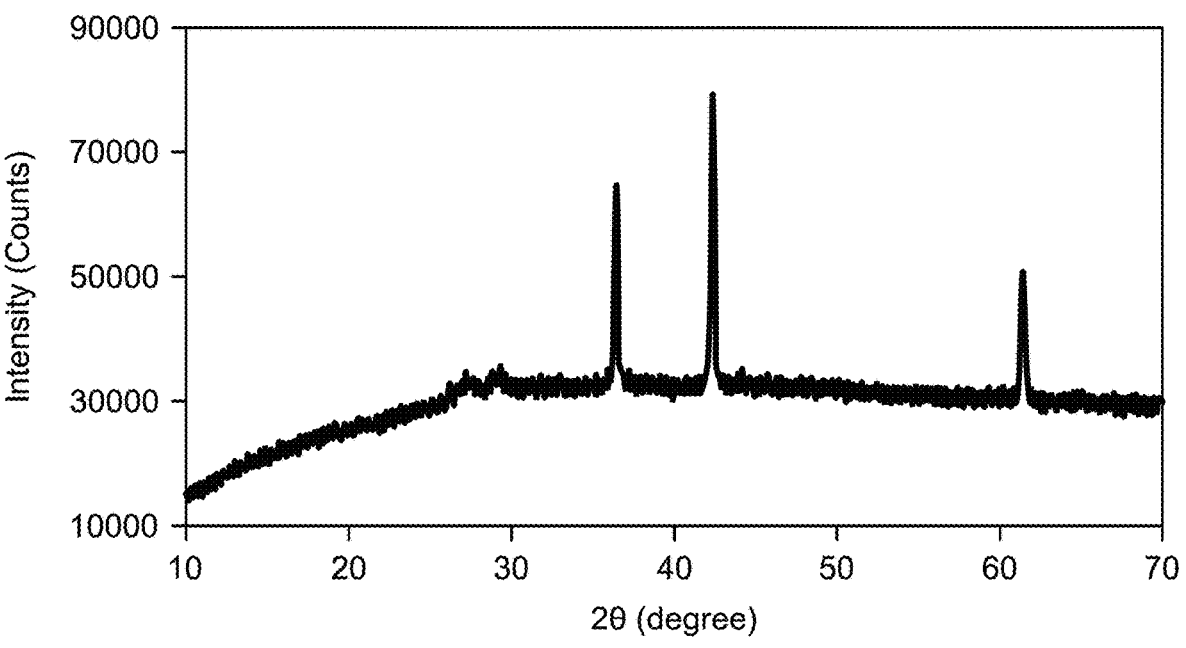
FIG. 1 shows X-ray diffractogram (XRD) of a $CoO/CaSiO_3@g\text{-}C_3N_4$ nanocomposite material, according to certain embodiments.

When describing the present disclosure, the terms used are to be construed in accordance with the following definitions, unless a context dictates otherwise.

Embodiments of the present disclosure will now be described more fully hereinafter with reference to the accompanying drawings wherever applicable, in that some, but not all, embodiments of the disclosure are shown.

In the drawings, like reference numerals designate identical or corresponding parts throughout the several views. Further, as used herein, the words 'a,' 'an, and the like generally carry a meaning of 'one or more,' unless stated otherwise.

Furthermore, the terms 'approximately,' 'approximate,' 'about,' and similar terms generally refer to ranges that include the identified value within a margin of 20 percent (%), 10%, or preferably 5%, and any values therebetween.

When amounts, concentrations, dimensions, and other parameters are expressed in the form of a range, a preferable range, an upper limit value, a lower limit value, or preferable upper and limit values, it should be understood that any ranges obtainable by combining any upper limit or preferable value with any lower limit or preferable value are also specifically disclosed, irrespective of whether the obtained ranges are clearly mentioned in the context.

In this application, a numerical value interval (i.e., a numerical value range) is involved, and, if not specifically stated, an optional numerical value distribution is considered continuous within the numerical value interval and includes two numerical value endpoints (i.e., minimum and maximum values) of the numerical value range and each numerical value between the two numerical value endpoints.

The temperature parameters in the present application, if not specifically limited, are both allowed to be constant temperature processing and allowed to be varied within a certain temperature interval. It should be understood that the constant temperature processing allows the temperature to fluctuate within the precision range of the instrument control. It is allowed to fluctuate in the range of, for example, 5° C., 4° C., 3° C., 2° C., 1° C.

A weight percent of a component, unless specifically stated to the contrary, is based on the total weight of the formulation or composition in which the component is included. For example, if a particular element or component in a composition or article is said to have 5 weight percent (wt. %), it is understood that this percentage is in relation to a total compositional percentage of 100%.

The present disclosure is intended to include all hydration states of a given compound or formula, unless otherwise noted or when heating a material.

In addition, the present disclosure is intended to include all isotopes of atoms occurring in the present compounds and complexes. Isotopes include those atoms having the same atomic number but different mass numbers. By way of general example, and without limitation, isotopes of hydrogen include deuterium and tritium, and isotopes of carbon include $^{13}C$ and $^{14}C$. Isotopes of oxygen include $^{16}O$, $^{17}O$, and $^{18}O$. Isotopically-labeled compounds of the disclosure may generally be prepared by conventional techniques known to those skilled in the art or by processes analogous to those described herein, using an appropriate isotopically-labeled reagent in place of the non-labeled reagent otherwise employed.

As used herein, the term 'pore diameter' refers to an average width or size of the pores (void spaces) within a material, typically measured in nm or angstroms (Å). It is a parameter in characterizing the texture and permeability of porous materials, influencing their adsorption, filtration, or catalytic properties. The pore diameter is often determined using methods such as nitrogen adsorption or mercury intrusion, which provide insights into the material's ability to absorb or interact with molecules of specific sizes.

As used herein, the term 'pore volume' refers to the total volume of void spaces (pores) within a material that is capable of being filled by a gas or liquid. It is typically expressed in cubic centimeters per gram ($cm^3/g$) and is an important parameter in characterizing the porous structure of materials, such as adsorbents or catalysts.

As used herein, the term 'cancer' refers to all types of cancer, neoplasm, or malignant tumors found in animals (e.g., humans), including leukemias, lymphomas, carcinomas, and sarcomas. Exemplary cancers that may be treated with a compound or method provided herein include brain cancer, glioma, glioblastoma, neuroblastoma, prostate cancer, colorectal cancer, pancreatic cancer, Medulloblastoma, melanoma, cervical cancer, gastric cancer, ovarian cancer, lung cancer, cancer of the head, Hodgkin's Disease, and Non-Hodgkin's Lymphomas. Exemplary cancers that may be treated with a compound or method provided herein include cancer of the thyroid, endocrine system, brain, breast, cervix, colon, head & neck, liver, kidney, lung, ovary, pancreas, rectum, stomach, and uterus. Additional examples include, thyroid carcinoma, cholangiocarcinoma, pancreatic adenocarcinoma, skin cutaneous melanoma, colon adenocarcinoma, rectum adenocarcinoma, stomach adenocarcinoma, esophageal carcinoma, head and neck squamous cell carcinoma, breast invasive carcinoma, lung adenocarcinoma, lung squamous cell carcinoma, non-small cell lung carcinoma, mesothelioma, multiple myeloma, neuroblastoma, glioma, glioblastoma multiforme, ovarian cancer, rhabdomyosarcoma, primary thrombocytosis, primary macroglobulinemia, primary brain tumors, malignant pancreatic insulanoma, malignant carcinoid, urinary bladder cancer, premalignant skin lesions, testicular cancer, thyroid cancer, neuroblastoma, esophageal cancer, genitourinary tract cancer, malignant hypercalcemia, endometrial cancer, adrenal cortical cancer, neoplasms of the endocrine or exocrine pancreas, medullary thyroid cancer, medullary thyroid carcinoma, melanoma, colorectal cancer, papillary thyroid cancer, hepatocellular carcinoma, or prostate cancer.

As used herein, the terms 'treat,' 'treatment,' and 'treating' in the context of the administration of a therapy to a subject in need thereof refer to the reduction or inhibition of the progression and or duration of cancer, the reduction or amelioration of the severity of cancer, and/or the amelioration of one or more symptoms thereof resulting from the administration of one or more therapies. The subject is a mammalian subject. In one embodiment, the subject is a human. 'Treating' or 'treatment' of a disease may include preventing the disease from occurring in a subject that may be predisposed to the disease but does not yet experience or exhibit symptoms of the disease (prophylactic treatment), inhibiting the disease (slowing or arresting its development), providing relief from the symptoms or side-effects of the disease (including palliative treatment), and relieving the disease (causing regression of the disease). With regard to cancer or hyperplasia, these terms simply mean that the life expectancy of an individual affected with cancer will be increased or that one or more of the symptoms of the disease will be reduced. In specific embodiments, such terms refer to one, two or three or more results following the administration of one, two, three or more therapies: (1) a stabilization, reduction or elimination of the cancer stem cell population; (2) a stabilization, reduction or elimination in the cancer cell population; (3) a stabilization or reduction in the growth of a tumor or neoplasm; (4) an impairment in the formation of a tumor; (5) eradication, removal, or control of primary, regional and/or metastatic cancer; (6) a reduction in mortality; (7) an increase in disease-free, relapse-free, progression-free, and/or overall survival, duration, or rate; (8) an increase in the response rate, the durability of response, or number of patients who respond or are in remission; (9) a decrease in hospitalization rate, (10) a decrease in hospitalization lengths, (11) the size of the tumor is maintained and does not increase or increases by less than 10%, preferably less than 5%, preferably less than 4%, preferably less than 2%, and (12) an increase in the number of patients in remission. In certain embodiments, such terms refer to a stabilization or reduction in cancer stem cell population. Such terms may refer to a stabilization or reduction in the growth of cancer cells. Such terms may refer to stabilization or reduction in cancer stem cell population and a reduction in the cancer cell population. Such terms refer to a stabilization or reduction in the growth and or formation of a tumor. Such terms may refer to the eradication, removal, or control of primary, regional, or metastatic cancer (e.g., the minimization or delay of the spread of cancer). Such terms may refer to a reduction in mortality and/or an increase in the survival rate of a patient population. Such terms may refer to an increase in the response rate, the durability of response, or the number of patients who respond or are in remission. Such terms may refer to a decrease in the hospitalization rate of a patient population and/or a decrease in hospitalization length for a patient population.

As used herein, the term 'contacting' means any way of effectively delivering the nanocomposite material to cancer cells, including but not limited to oral administration, administration as a suppository, topical contact, intravenous, parenteral, intraperitoneal, intramuscular, intralesional, intrathecal, intranasal, or subcutaneous administration, or the implantation of a slow-release device, e.g., a mini-osmotic pump, to a subject. Contacting is by any route, including parenteral and transmucosal (e.g., buccal, sublingual, palatal, gingival, nasal, vaginal, rectal, or transdermal). Parenteral contacting may include, e.g., intravenous, intramuscular, intra-arteriole, intradermal, subcutaneous, intraperitoneal, intraventricular, and intracranial. Other modes of delivery include, but are not limited to, the use of liposomal formulations, intravenous infusion, transdermal patches, etc.

As used herein, the term 'cell viability' refers to the proportion of live, healthy cells in a population after being exposed to various conditions or treatments. It is commonly measured to assess the health and functionality of cells in laboratory studies, particularly when testing the effects of drugs, toxins, or other experimental variables. Viable cells can maintain their metabolism, growth, and division processes, while non-viable cells are damaged, dysfunctional, or dead. Cell viability is often assessed using assays that measure metabolic activity, membrane integrity, or other indicators of cellular health.

As used herein, the term 'nanoparticles (NPs)' refers to particles having a particle size of 1 nanometer (nm) to 1000 nm within the scope of the present disclosure.

As used herein, the term 'nanocomposite' is a material that is made by combining a matrix (often a polymer, metal, or ceramic) with NPs or nanomaterials to enhance its properties. The NPs are typically on the scale of nm (1 to 1000 nm), and their small size and high surface area can significantly improve the composite material's strength, thermal stability, electrical conductivity, optical properties, and other characteristics.

As used herein, percent inhibition refers to how much cancer cell growth has been reduced by a treatment compared to a control group. It is typically determined by comparing the number of cells in a treated group to a non-treated group, and is expressed as a percentage, where a higher percentage of inhibition indicates a greater reduction in cell growth. For example, a 50% inhibition of cancer cell growth means that 50% of the cancer cells proliferated in the treated group as compared to the control.

As used herein, the term 'half maximal inhibitory concentration ($IC_{50}$)' refers to the measure of the potency of a substance in inhibiting a specific biological or biochemical function. $IC_{50}$ is a quantitative measure that indicates how much of a particular inhibitory substance (e.g., drug) is needed to inhibit, in vitro, a given biological process or biological component by 50%. The biological component can be an enzyme, cell, cell receptor or microorganism. $IC_{50}$ values are typically expressed as molar concentration.

As used herein, the term 'HepG-2 human hepatocellular carcinoma cells' refer to a type of cancer cell line derived from a liver tumor in a human patient.

As used herein, the term 'MCF-7 human breast carcinoma cells' refer to cell line derived from a breast cancer tumor.

Aspects of the present disclosure are directed to a method of treating cancer using a nanocomposite material including cobalt oxide (CoO), calcium silicate ($CaSiO_3$), and graphitic carbon nitride ($g$-$C_3N_4$). When each component of the nanocomposite material is used in appropriate ratios assembled in an appropriate morphology, the nanocomposite material can effectively kill cancer cells via an apoptotic pathway.

According to a first aspect of the present disclosure, a method of treating cancer cells is described. The method includes contacting the cancer cells with the nanocomposite material in an amount sufficient to kill the cancer cells.

In one or more embodiments, the nanocomposite material includes hexagonal metal oxide nanoparticles consisting of a $CoO$ phase and a $CaSiO_3$ phase dispersed on a matrix of g-$C_3N_4$ nanosheets. In one or more embodiments, the hexagonal metal oxide nanoparticles have an average particle diameter in a range from 310 to 470 nm, preferably 340 to 440 nm, preferably 350 to 430 nm, preferably 360 to 420 nm. In some embodiments, the hexagonal metal oxide nanoparticles have an average particle diameter in a range from 370-410 nm, preferably 371-409 nm, preferably 372-408 nm, preferably 373-407 nm, preferably 374-406 nm, preferably 375-405 nm, preferably 376-404 nm, preferably 377-403 nm, preferably 378-402 nm, preferably 379-401 nm, preferably 380-400 nm, preferably 381-399 nm, preferably 382-398 nm, preferably 383-397 nm, preferably 384-396 nm, preferably 385-395 nm and preferably 386-394 nm.

In some embodiments, the hexagonal metal oxide nanoparticles have an average particle diameter in a range from 380-400 nm, preferably 381-399 nm, preferably 382-398 nm, preferably 383-397 nm, preferably 384-396 nm, preferably 385-395 nm, and preferably 386-394 nm. In some embodiments, the hexagonal metal oxide nanoparticles have an average particle diameter in a range from 382-395 nm, preferably 383-394 nm, preferably 384-393 nm, preferably 385-392 nm and preferably 386-391 nm. In a preferred embodiment, the hexagonal metal oxide nanoparticles have an average particle diameter of 387 nm.

In one or more embodiments, the $CoO$/$CaSiO_3$@g-$C_3N_4$ nanocomposite material has a mass ratio of the $CoO$:$CaSiO_3$:g-$C_3N_4$ phases in a range from 0.25-10:0.25-10:0.25:10, preferably 0.5-7.5:0.5-7.5:0.5-7.5, preferably 1-5:1-5:1-5.

The BET hypothesis is the foundation for a useful analysis method for determining the specific surface area of a material. Specific surface area is a property of solids, which is the total surface area of a material per unit of mass, solid or bulk volume, or cross-sectional area. In some embodiments, pore diameter, pore volume, and BET surface area are measured by gas adsorption analysis, preferably $N_2$ adsorption analysis (e.g., $N_2$ adsorption isotherms).

In some embodiments, the average pore distribution of the nanocomposite may include, but is not limited to, crystalline average pore distribution, bimodal, trimodal, multimodal, narrow, broad, and Gaussian. In a preferred embodiment, the average pore distribution of nanocomposite is unimodal, indicating a single dominant pore population within the material. This unimodal distribution indicates that the nanocomposite material possess a relatively narrow pore size range, resulting in more uniform pore structures and possibly enhancing specific properties such as adsorption capacity, catalytic activity, and surface reactivity.

In some embodiments, the nanocomposite material has a BET surface area of at least 10 square meters per gram ($m^2 \cdot g^{-1}$), preferably 20 $m^2 \cdot g^{-1}$, preferably at least 20.5 $m^2 \cdot g^{-1}$, preferably at least 21 $m^2 \cdot g^{-1}$, preferably at least 21.5 $m^2 \cdot g^{-1}$, preferably at least 22 $m^2 \cdot g^{-1}$, preferably at least 22.5 $m^2 \cdot g^{-1}$, preferably at least 23.5 $m^2 \cdot g^{-1}$, preferably at least 24 $m^2 \cdot g^{-1}$, preferably at least 24.5 $m^2 \cdot g^{-1}$, preferably at least 25 $m^2 \cdot g^{-1}$, preferably at least 25.5

$m^2 \cdot g^{-1}$, preferably at least 26 $m^2 \cdot g^{-1}$, preferably at least 26.5 $m^2 \cdot g^{-1}$, preferably at least 27 $m^2 \cdot g^{-1}$, preferably at least 27.5 $m^2 \cdot g^{-1}$, preferably at least 28 $m^2 \cdot g^{-1}$, preferably at least 28.5 $m^2 \cdot g^{-1}$, preferably at least 29 $m^2 \cdot g^{-1}$, preferably at least 29.5 $m^2 \cdot g^{-1}$, preferably at least 29.6 $m^2 \cdot g^{-1}$, preferably at least 29.7 $m^2 \cdot g^{-1}$, preferably at least 29.8 $m^2 \cdot g^{-1}$, preferably at least 29.9 $m^2 \cdot g^{-1}$, preferably at least 30 $m^2 \cdot g^{-1}$, preferably at least 30.1 $m^2 \cdot g^{-1}$, preferably at least 30.2 $m^2 \cdot g^{-1}$, preferably at least 30.3 $m^2 \cdot g^{-1}$, preferably at least 30.4 $m^2 \cdot g^{-1}$ and preferably at least 30.5 $m^2 \cdot g^{-1}$.

In some embodiments, the nanocomposite material has a BET surface area of at least 25 $m^2 \cdot g^{-1}$, preferably at least 25.5 $m^2 \cdot g^{-1}$, preferably at least 25.6 $m^2 \cdot g^{-1}$, preferably at least 25.7 $m^2 \cdot g^{-1}$, preferably at least 25.8 $m^2 \cdot g^{-1}$, preferably at least 25.9 $m^2 \cdot g^{-1}$, preferably at least 30 $m^2 \cdot g^{-1}$, preferably at least 30.1 $m^2 \cdot g^{-1}$, preferably at least 30.2 $m^2 \cdot g^{-1}$, preferably at least 30.3 $m^2 \cdot g^{-1}$, preferably at least 30.4 $m^2 \cdot g^{-1}$ and preferably at least 30.5 $m^2 \cdot g^{-1}$.

In some embodiments, nanocomposite material has a BET surface area of at least 30 $m^2 \cdot g^{-1}$, preferably at least 30.1 $m^2 \cdot g^{-1}$, preferably at least 30.2 $m^2 \cdot g^{-1}$, preferably at least 30.3 $m^2 \cdot g^{-1}$, preferably at least 30.4 $m^2 \cdot g^{-1}$ and preferably at least 30.5 $m^2 \cdot g^{-1}$. In a preferred embodiment, the nanocomposite material has a BET surface area of 30.68 $m^2 \cdot g^{-1}$.

In some embodiments, the nanocomposite material has a pore volume of at least 0.05 $cm^3 \cdot g^{-1}$, preferably at least 0.10 $cm^3 \cdot g^{-1}$, preferably at least 0.11 $cm^3 \cdot g^{-1}$, preferably at least 0.12 $cm^3 \cdot g^{-1}$, preferably at least 0.13 $cm^3 \cdot g^{-1}$, preferably at least 0.14 $cm^3 \cdot g^{-1}$, preferably at least 0.15 $cm^3 \cdot g^{-1}$, preferably at least 0.16 $cm^3 \cdot g^{-1}$, preferably at least 0.17 $cm^3 \cdot g^{-1}$, preferably at least 0.18 $cm^3 \cdot g^{-1}$, preferably at least 0.19 $cm^3 \cdot g^{-1}$, preferably at least 0.191 $cm^3 \cdot g^{-1}$, preferably at least 0.192 $cm^3 \cdot g^{-1}$, preferably at least 0.193 $cm^3 \cdot g^{-1}$, preferably at least 0.194 $cm^3 \cdot g^{-1}$ and preferably at least 0.195 $cm^3 \cdot g^{-1}$ In some embodiments, the nanocomposite material has a pore volume of at least 0.15 $cm^3 \cdot g^{-1}$, preferably at least 0.152 $cm^3 \cdot g^{-1}$, preferably at least 0.156 $cm^3 \cdot g^{-1}$, preferably at least 0.158 $cm^3 \cdot g^{-1}$, preferably at least 0.160 $cm^3 \cdot g^{-1}$, preferably at least 0.162 $cm^3 \cdot g^{-1}$, preferably at least 0.164 $cm^3 \cdot g^{-1}$, preferably at least 0.166 $cm^3 \cdot g^{-1}$, preferably at least 0.168 $cm^3 \cdot g^{-1}$, preferably at least 0.17 $cm^3 \cdot g^{-1}$, preferably at least 0.172 $cm^3 \cdot g^{-1}$, preferably at least 0.174 $cm^3 \cdot g^{-1}$, preferably at least 0.176 $cm^3 \cdot g^{-1}$, preferably at least 0.178 $cm^3 \cdot g^{-1}$, preferably at least 0.18 $cm^3 \cdot g^{-1}$, preferably at least 0.182 $cm^3 \cdot g^{-1}$, preferably at least 0.184 $cm^3 \cdot g^{-1}$, preferably at least 0.186 $cm^3 \cdot g^{-1}$, preferably at least 0.188 $cm^3 \cdot g^{-1}$, preferably at least 0.19 $cm^3 \cdot g^{-1}$, preferably at least 0.191 $cm^3 \cdot g^{-1}$, preferably at least 0.192 $cm^3 \cdot g^{-1}$, preferably at least 0.193 $cm^3 \cdot g^{-1}$, preferably at least 0.194 $cm^3 \cdot g^{-1}$ and preferably at least 0.195 $cm^3 \cdot g^{-1}$. In a preferred embodiment, the nanocomposite material has a pore volume of at least 0.195 $cm^3 \cdot g^{-1}$.

In some embodiments, the nanocomposite material has an average pore diameter in a range from 1-40 nm, preferably 10-30 nm, preferably 11-29.9 nm, preferably 11.5-29.8 nm, preferably 12-29.7 nm, preferably 12.5-29.6 nm, preferably 13-29.5 nm, preferably 13.5-29.4 nm, preferably 14-29.3 nm, preferably 14.5-29.2 nm, preferably 15-29.1 nm, preferably 15.5-29.0 nm, preferably 16-28.9 nm, preferably 16.5-28.8 nm, preferably 17-28.7 nm, preferably 17.5-28.6 nm, preferably 18-28.5 nm, preferably 18.5-28.4 nm, preferably 19-28.3 nm, preferably 19.5-28.2 nm, preferably 20-28.1 nm, preferably 20.5-28 nm and preferably 21-27 nm.

In some embodiments, the nanocomposite material has an average pore diameter in a range from 15-27 nm, preferably 15.1-26.9 nm, preferably 15.3-26.7 nm, preferably 15.5-26.5 nm, preferably 15.7-26.3 nm, preferably 15.9-26.1 nm, preferably 16.1-25.9 nm, preferably 16.3-25.7 nm, preferably 16.5-25.5 nm, preferably 16.7-25.3 nm, preferably 16.9-25.1 nm, preferably 17.1-24.9 nm, preferably 17.3-24.7 nm, preferably 17.5-24.5 nm, preferably 17.7-24.3 nm, preferably 17.9-24.1 nm, preferably 18.1-23.9 nm, preferably 18.3-23.7 nm, preferably 18.5-23.5 nm, preferably 18.7-23.3 nm, preferably 18.9-23.1 nm, preferably 19.1-22.9 nm, preferably 19.3-22.7 nm, preferably 19.5-22.5 nm, preferably 19.7-22.3 nm, preferably 19.9-22.1 nm and preferably 20.1-21.9 nm. In a preferred embodiment, the nanocomposite material has an average pore diameter of 21.82 nm.

In one or more embodiments, the $CoO/CaSiO_3@g-C_3N_4$ nanocomposite material has a percent inhibition for human Breast carcinoma (MCF-7) cells of at least 40%, preferably at least 55%, preferably at least 60%, preferably at least 65%, preferably at least 70%, preferably at least 75%, preferably about 77% inhibition in an in-vitro cellular viability assay.

In one or more embodiments, the $CoO/CaSiO_3@g-C_3N_4$ nanocomposite material has a percent inhibition for Human Hepatocellular Carcinoma (HepG-2) cells of at least 45%, preferably at least 60%, preferably at least 65%, preferably at least 70%, preferably at least 75%, preferably about 76% inhibition in an in-vitro cellular viability assay.

EXAMPLES

The following examples demonstrate a method of treating cancer using the $CoO/CaSiO_3@g-C_3N_4$ nanocomposite material. The examples are provided solely for illustration and are not to be construed as limitations of the present disclosure, as many variations thereof are possible without departing from the spirit and scope of the present disclosure.

Example 1: Fabricating the $CaSiO_3$

Equal moles of calcium nitrate (0.5 g) and sodium metasilicate (0.37 g) were dispersed in 100 milliliters (mL) of ethanol:water (1:1) in a 150 mL glass beaker and sonicated for 15 minutes. The mixture was transferred to a 200 mL autoclave and then placed in an oven operated at 180° C. for 2 hours. The product was dispersed in 500 mL distilled water with an ultrasonic bath for 10 minutes, filtered via a Buchner system, rinsed with distilled water, and dried at 120° C. for 1 hour.

Example 2: Fabricating the $g-C_3N_4$

About 30 grams (g) of urea ($NH_2CONH_2$) was placed in a 250 milliliters (mL) porcelain crucible and covered with its porcelain cover, then the crucible and cover were wrapped with three layers of aluminum foil to reduce the $NH_2CONH_2$ loss to sublimation. The crucible was heated via a furnace set at 600° C. for 45 min.

Example 3: Fabricating the CoO

About 10 g of cobalt (II) acetate ($C_4H_6CoO_4$) and 5 g of xylose ($C_5H_{10}O_5$) were placed in a 500 mL beaker. 100 mL distilled water was added to the mixture and heated until a clear solution was obtained. 10 mL of concentrated nitric acid ($HNO_3$) was added to the mixture, which was then heated until the carbonization of $C_5H_{10}O_5$. The mixture was placed in an oven set at 120° C. for 3 h; the black product was milled in a mortar, placed in a 150 mL porcelain dish, and calcined at 550° C. for 4 h.

Example 4: Fabricating the $CoO/CaSiO_3@g-C_3N_4$

An equal amount of calcium silicate ($CaSiO_3$), graphitic carbon nitride ($g-C_3N_4$), and cobalt oxide (CoO) (0.5 grams each) was transferred to a mono wave-200 vial (G30), dispersed in 20 mL ethylene glycol monomethyl ether via an ultrasonic bath for 30 min. The vial was closed with its teflon cover and placed in the Anton-Baar Monowave-200 operated at 180° C. and 5 bar pressure for one hour. The product was dispersed in 1 L distilled water with an ultrasonic bath for 30 min, filtered via a Buchner system, rinsed with distilled water, and dried at 150° C. for 2 h.

Example 5: Anticancer Activity

Cell line Propagation: The cells were grown on RPMI-1640 medium supplemented with 10% inactivated fetal calf serum and 50 µg/ml gentamycin. The cells were maintained at 37° C. in a humidified atmosphere with 5% $CO_2$ and were sub-cultured two to three times a week.

Example 6: Cytotoxicity Evaluation Using Viability Assay

For antitumor assays, the tumor cell lines were suspended in a medium at a concentration of $5×10^4$ cell/well in Coming 96-well tissue culture plates, then incubated for 24 hr. The tested compounds were then added into 96-well plates (three replicates) to achieve ten concentrations for each compound. Six vehicle controls with media were run for each 96-well plate as a control. After incubating for 24 h, the numbers of viable cells were determined by the MTT test. Briefly, the media was removed from the 96 well plates and replaced with 100 µl of fresh culture RPMI 1640 medium without phenol red, then 10 µl of the 12 mM MTT stock solution (5 mg of MTT in 1 mL of PBS) was added to each well, including the untreated controls. The 96-well plates were incubated at 37° C. and 5% $CO_2$ for 4 hours. An 85 µl aliquot of the media was removed from the wells, and 50 µl of DMSO was added to each well, mixed thoroughly with the pipette, and then incubated at 37° C. for 10 min. Then, the optical density was measured at 590 nm with the microplate reader (Sunrise, TECAN, Inc., USA) to determine the number of viable cells. The percentage of viability was calculated as [(ODt/ODc)]×100%, where ODt is the mean optical density of wells treated with the tested sample and ODc is the mean optical density of untreated cells. The relation between surviving cells and drug concentration is plotted to get the survival curve of each tumor cell line after treatment with the specified compound. The 50% inhibitory concentration ($IC_{50}$) required to cause toxic effects in 50% of intact cells was estimated from graphic plots of the dose-response curve for each concentration using GraphPad Prism software (San Diego, CA).

XRD was used to examine the crystallinity and phase identification of the $CoO/CaSiO_3@g-C_3N_4$ catalyst and the findings are shown in FIG. 1. The powder's high crystalline nature is shown by its sharp peaks and high intensity values. CoO is present as a primary phase together with $CaSiO_3$ and $g-C_3N_4$ as minor phases, according to an analysis of the diffraction patterns using standard JCPDS cards. The sharp peaks located at 2θ values of 36.5, 42.4, 61.5, 73.6, and 77.5° were well used to index the CoO cubic phase. These diffractions originated respectively from (111), (200), (220), (311), and (222) plans of the cubic phase of CoO (Reference code No. 01-071-1178). Weak diffractions at $2\ominus$ values of 27.6, and 28.9° were used to detect the $CaSiO_3$ phase (Reference code No. 01-084-0655). Traces of quartz $SiO_2$ were detected at 20 value of 27.3° (Reference code No. 01-079-1911). The $g$-$C_3N_4$ diffractions were recorded at 61.4° (Reference code No. 01-087-1526). $CoO/CaSiO_3@g$-$C_3N_4$ was successfully fabricated since no further phases were found.

Figure 2A:
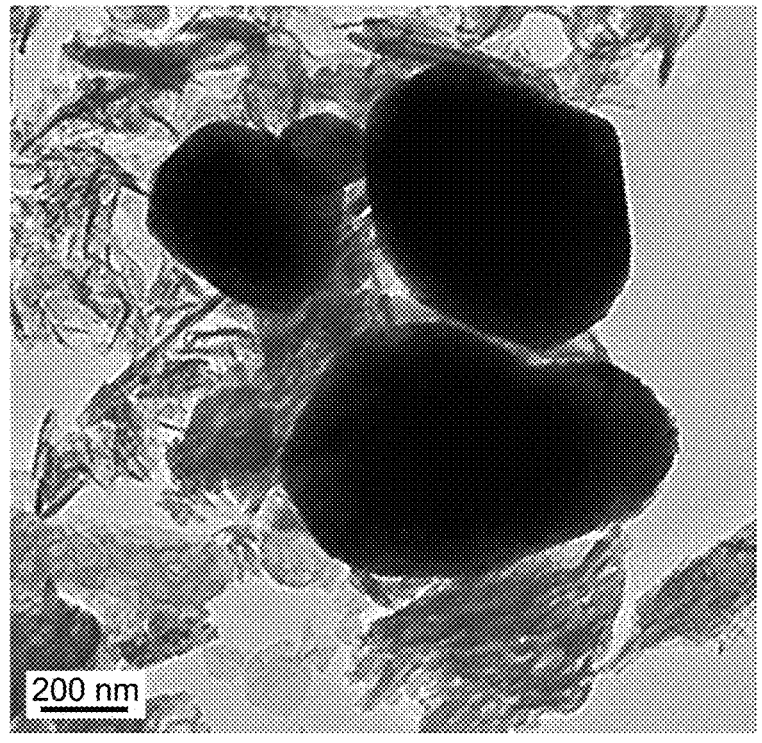
FIG. 2A is a transmission electron microscopy (TEM) image of the $CoO/CaSiO_3@g\text{-}C_3N_4$ nanocomposite material, at 200 nanometers (nm) magnification, according to certain embodiments.
Figure 2B:
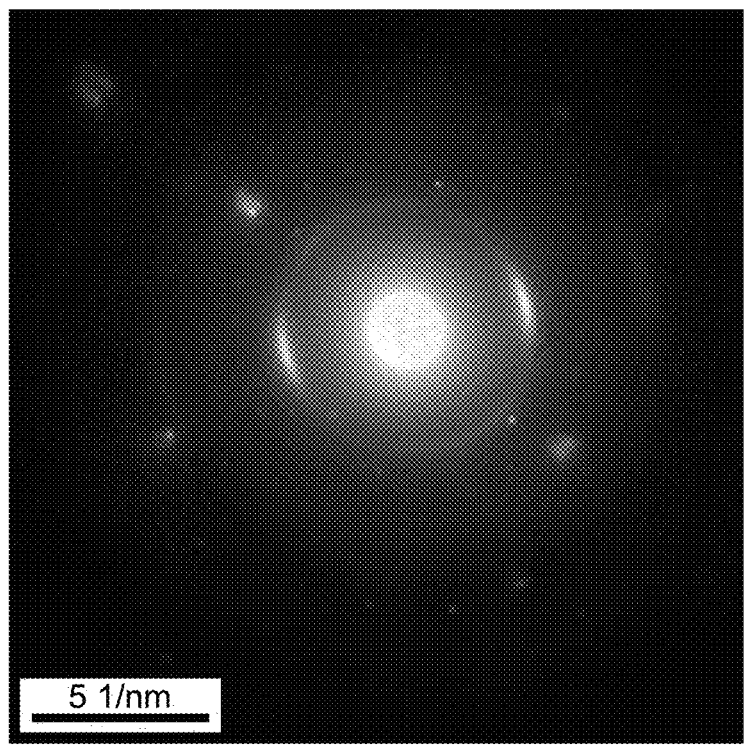
FIG. 2B is a selected area electron diffraction (SAED) pattern of the $CoO/CaSiO_3@g\text{-}C_3N_4$ nanocomposite material, according to certain embodiments.

TEM images of the $CoO/CaSiO_3@g$-$C_3N_4$ nanocomposite are presented in FIG. 2A. The TEM images show that a two-dimensional porous structure was constructed with curled and wrinkled nanosheets and platelets of the $g$-$C_3N_4$ (FIG. 2A). The image shows also well dispersed homogeneous hexagonal shaped metal oxides nanoparticles with a size of 387 nm on nanosheets of $g$-$C_3N_4$. The corresponding SAED pattern reveals diffraction spots with interplanar spacing of 0.288 nm, 0.256 nm, and 0.186 nm, 0.142 nm due to ($CaSiO_3$: 131), (CoO: 111, $CaSiO_3$: 022), ($CaSiO_3$: -2-32), and (CoO: 220, $CaSiO_3$: -330, $g$-$C_3N_4$; 221) diffraction planes (FIG. 2B).

Figure 3A:
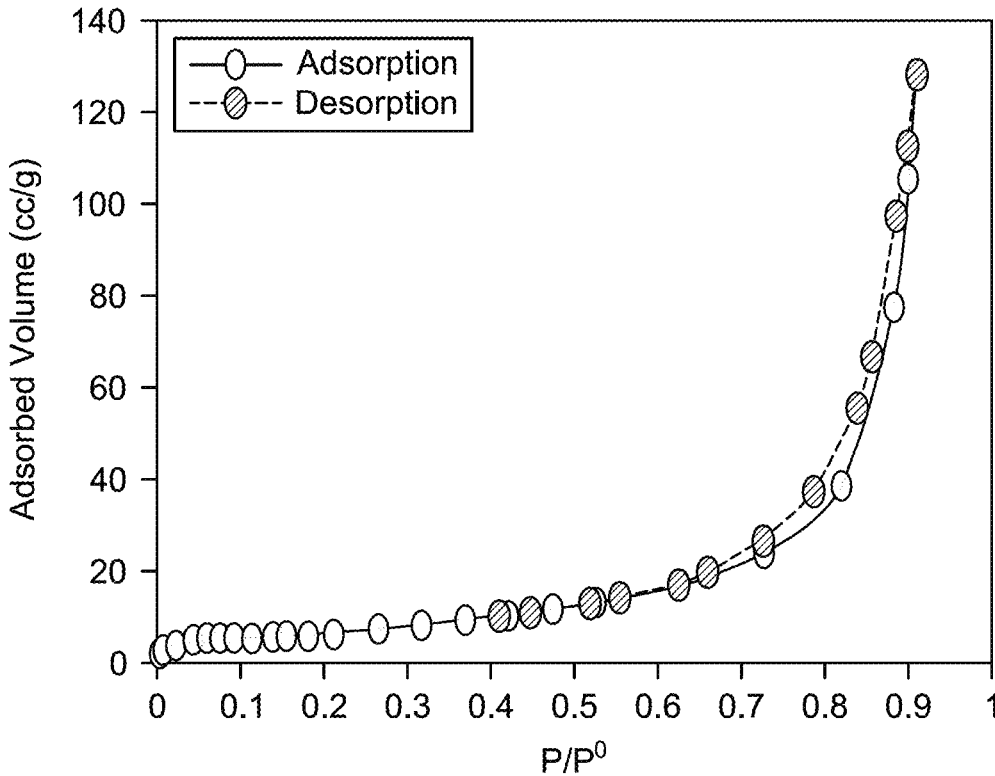
FIG. 3A is a graph depicting nitrogen adsorption-desorption isotherm of the $CoO/CaSiO_3@g\text{-}C_3N_4$ nanocomposite material, according to certain embodiments.
Figure 3B:
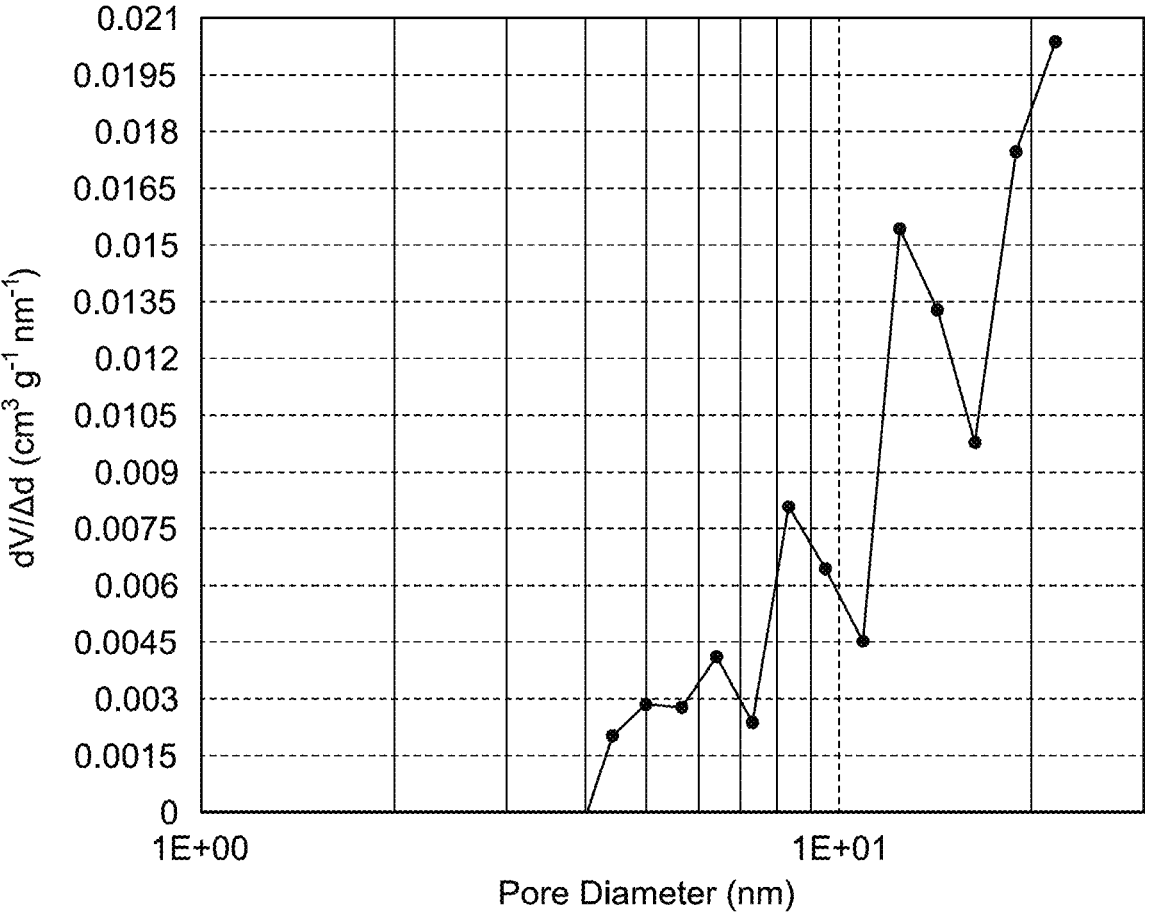
FIG. 3B is a graph depicting the pore size distribution of the $CoO/CaSiO_3@g\text{-}C_3N_4$ nanocomposite material, according to certain embodiments.

FIG. 3A displays the nitrogen adsorption-desorption isotherms of the $CoO/CaSiO_3@g$-$C_3N_4$ nanocomposite. The nitrogen sorption isotherm of the composite belongs to type IV with a noticeable hysteresis loop, indicating the formation of mesoporous structures. However, shifting the loop to a relatively higher pressure (P/P0=0.66-1) indicates the presence of wide mesopores, which may result from the deposition of metal oxide particles in the wide pores of $g$-$C_3N_4$. Furthermore, the BET surface area of the $CoO/CaSiO_3@g$-$C_3N_4$ sample was calculated to be 30.68 $m^2 g^{-1}$. The marked high specific surface area reflects the good dispersion of these metal oxide nanoparticles on $g$-$C_3N_4$. and $CaSiO_3$. Moreover, the pore size distribution curves, plotted using the BJH method, for the $CoO/CaSiO_3@g$-$C_3N_4$ sample exhibited unimodal distribution with average pore diameters maximized at 21.82 nm and a pore volume of 0.198 $cm^3 g^{-1}$. All the isotherms belong to the category H3 type of pores, which do not exhibit limiting adsorption at high P/P°, and arise due to the aggregation of plate-like particles, giving rise to slit-shaped pores. This indicates that the assembly of $CoO/CaSiO_3@g$-$C_3N_4$ composite produced a mesoporous array (FIG. 3B).

Figure 3C:
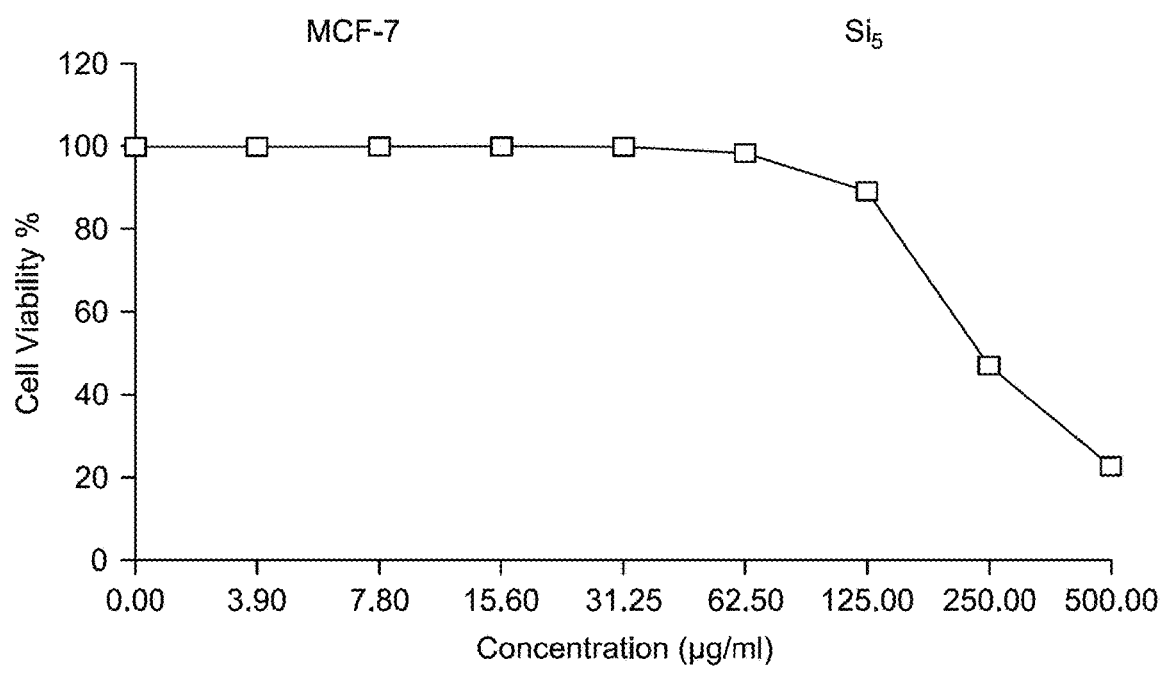
FIG. 3C is a graph depicting the inhibitory activity of the $CoO/CaSiO_3@g\text{-}C_3N_4$ nanocomposite material against MCF-7 cells, according to certain embodiments.

An in-vitro investigation was conducted for the $CoO/CaSiO_3@g$-$C_3N_4$ nanocompisite material against the Human Hepatocellular Carcinoma (HepG-2) and Human Breast carcinoma cell lines (MCF-7). A concentration range of 3.0 to 500 g/ml $CoO/CaSiO_3@g$-$C_3N_4$ was used and the obtained results against the MCF-7 cell line are illustrated in FIG. 3C. The MCF-7 cell's viability started declining with only a 62.5 µg/ml $CoO/CaSiO_3@g$-$C_3N_4$ dose, the $IC_{50}$ was 241.26 µg/ml, and the maximum dose (500 µg/ml) showed a 77.0% inhibition of the MCF-7 cells (FIG. 3C).

Figure 3D:
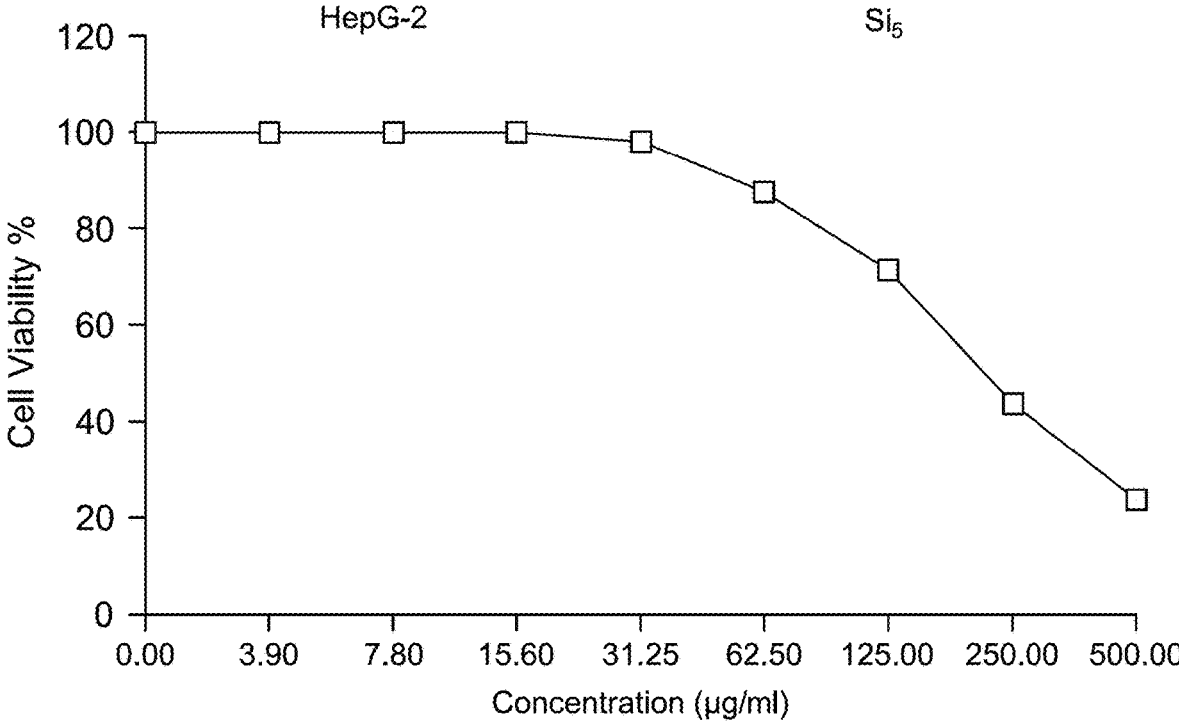
FIG. 3D is a graph depicting the inhibitory activity of the $CoO/CaSiO_3@g\text{-}C_3N_4$ nanocomposite material against HepG-2 cells, according to certain embodiments.

Furthermore, a concentration range of 3.0 to 500 g/ml $CoO/CaSiO_3@g$-$C_3N_4$ was applied against the HepG-2 cell line and the obtained results are illustrated in FIG. 3D. The HepG-2 cell's viability started declining with only a 31.5 g/ml $CoO/CaSiO_3@g$-$C_3N_4$ dose, the $IC_{50}$ was 221.62 µg/ml, and the maximum dose (500 g/ml) showed a 76% inhibition of the HepG-2 cells (FIG. 3D).

Numerous modifications and variations of the present disclosure are possible in light of the above teachings. It is, therefore, to be understood that within the scope of the appended claims, the disclosure may be practiced otherwise than as specifically described herein.

The invention claimed is:

1. A method of treating breast or liver cancer cells, comprising:
   contacting the breast or liver cancer cells with a $CoO/CaSiO_3@g$-$C_3N_4$ nanocomposite material,
   wherein the $CoO/CaSiO_{3@4}g$-$C_3N_4$ nanocomposite material comprises hexagonal metal oxide nanoparticles comprising a CoO phase and a $CaSiO_3$ phase dispersed on a matrix of $g$-$C_3N_4$ nanosheets,
   wherein the hexagonal metal oxide nanoparticles have an average particle diameter in a range from 340 to 440 nm,
   wherein the $CoO/CaSiO_3@g$-$C_3N_4$ nanocomposite material has a percent inhibition for Human Breast Carcinoma (MCF-7) cells of at least 55% inhibition in an in-vitro cellular viability assay, and
   wherein the $CoO/CaSiO_3Lg$-$C_3N_4$ nanocomposite material has a percent inhibition for Human Hepatocellular Carcinoma (HepG-2) cells of at least 60% inhibition in an in-vitro cellular viability assay.

2. The method of claim 1, wherein the $CoO/CaSiO_3@g$-$C_3N_4$ nanocomposite material has a percent inhibition for MCF-7 cells of at least 60% inhibition in an in-vitro cellular viability assay.

3. The method of claim 2, wherein the $CoO/CaSiO_3@6g$-$C_3N_4$ nanocomposite material has a percent inhibition for MCF-7 cells of at least 65% inhibition in an in-vitro cellular viability assay.

4. The method of claim 3, wherein the $CoO/CaSiO_3@g$-$C_3N_4$ nanocomposite material has a percent inhibition for MCF-7 cells of at least 70% inhibition in an in-vitro cellular viability assay.

5. The method of claim 4, wherein the $CoO/CaSiO_3@g$-$C_3N_4$ nanocomposite material has a percent inhibition for MCF-7 cells of at least 75% inhibition in an in-vitro cellular viability assay.

6. The method of claim 5, wherein the $CoO/CaSiO_3@g$-$C_3N_4$ nanocomposite material has a percent inhibition for MCF-7 cells of 77% inhibition in an in-vitro cellular viability assay.

7. The method of claim 1, wherein the $CoO/CaSiO_3@(g$-$C_3N_4$ nanocomposite material has a percent inhibition for HepG-2 cells of at least 65% inhibition in an in-vitro cellular viability assay.

8. The method of claim 7, wherein the $CoO/CaSiO_3@g$-$C_3N_4$ nanocomposite material has a percent inhibition for HepG-2 cells of at least 70% inhibition in an in-vitro cellular viability assay.

9. The method of claim 8, wherein the $CoO/CaSiO_3@g$-$C_3N_4$ nanocomposite material has a percent inhibition for HepG-2 cells of at least 75% inhibition in an in-vitro cellular viability assay.

10. The method of claim 9, wherein the $CoO/CaSiO_3@g$-$C_3N_4$ nanocomposite material has a percent inhibition for HepG-2 cells of 76% inhibition in an in-vitro cellular viability assay.

11. The method of claim 1, wherein the hexagonal metal oxide nanoparticles have an average particle diameter in a range from 370 to 410 nm.

12. The method of claim 11, wherein the hexagonal metal oxide nanoparticles have an average particle diameter in a range from 380 to 400 nm.

13. The method of claim 1, wherein the $CoO/CaSiO_3@g$-$C_3N_4$ nanocomposite material has a BET surface area of at least 20 $m^2 \cdot g^{-1}$.

14. The method of claim 13, wherein the $CoO/CaSiO_3@g$-$C_3N_4$ nanocomposite material has a BET surface area of at least 25 $m^2 \cdot g^{-1}$.

15. The method of claim 1, wherein the CoO/CaSiO$_3$@g-C$_3$N$_4$ nanocomposite material has a BET surface area of at least 30 m$^2 \cdot$g$^{-1}$.

16. The method of claim 1, wherein the CoO/CaSiO$_3$@g-C$_3$N$_4$ nanocomposite material has a pore volume of at least 0.10 cm$^3 \cdot$g$^{-1}$.

17. The method of claim 16, wherein the CoO/CaSiO$_3$@g-C$_3$N$_4$ nanocomposite material has a pore volume of at least 0.15 cm$^3 \cdot$g$^{-1}$.

18. The method of claim 17, wherein the CoO/CaSiO$_3$@g-C$_3$N$_4$ nanocomposite material has a pore volume of at least 0.195 cm$^3 \cdot$g$^{-1}$.

19. The method of claim 1, wherein the CoO/CaSiO$_3$@g-C$_3$N$_4$ nanocomposite material has an average pore diameter of 21.82 nm.

* * * * *